United States Patent [19]

Molinski et al.

[11] 3,987,157

[45] Oct. 19, 1976

[54] TECHNETIUM 99-M LABELED RADIO-DIAGNOSTIC AGENTS EMPLOYING STANNOUS TARTRATE AND METHOD OF PREPARATION

[75] Inventors: Victor J. Molinski, Ridgewood, N.J.; Joseph A. Wilczewski, Newburgh, N.Y.

[73] Assignee: Union Carbide Corporation, New York, N.Y.

[22] Filed: Aug. 29, 1974

[21] Appl. No.: 501,704

[52] U.S. Cl. .............................. 424/1; 252/301.1 R; 260/429 R
[51] Int. Cl.² .................. A61K 43/00; A61K 29/00
[58] Field of Search .............................. 424/1, 198; 252/301.1 R; 260/429 R

[56] References Cited
UNITED STATES PATENTS 3,735,001    5/1973    McRae et al. ........................ 424/1
3,852,414    12/1974   Adler et al. ........................... 424/1

FOREIGN PATENTS OR APPLICATIONS 2,244,463    4/1975    France ................................. 424/1

OTHER PUBLICATIONS

Gwyther et al., International Journal of Applied Radiation and Isotopes, vol. 17, Aug. 1966, pp. 485–486.
Subramanian et al., Radiology, vol. 102, Mar. 1972, pp. 701–704.
Castronova, Jr., et al., Journal of Nuclear Mediane, vol. 13, No. 11, 1972, pp. 823–827.

*Primary Examiner*—Benjamin R. Padgett
*Assistant Examiner*—Christine M. Nucker
*Attorney, Agent, or Firm*—Israel Blum

[57]    ABSTRACT

A method of preparing improved technetium-99m labeled radiodiagnostic agents by reducing technetium-99m with stannous tartrate. Such radiodiagnostic agents are useful in scintigraphic examinations of the bone and lung.

31 Claims, No Drawings

TECHNETIUM 99-M LABELED RADIO-DIAGNOSTIC AGENTS EMPLOYING STANNOUS TARTRATE AND METHOD OF PREPARATION

Field of the Invention

This invention relates to improved technetium-99m labeled radiodiagnostic agents useful in lung and bone scanning applications and a method for their preparation. In another aspect, this invention relates to non-radioactive carriers employing stannous tartrate as a reducing agent and a process for their preparation.

Description of the Prior Art

Technetium-99m has become an extremely useful tool in medical applications, particularly as a radionuclide tracer in both medical research and diagnosis. Technetium-99m's short half-life (6 hours) reduces exposure of the organs to radiation; its gamma radiation energy (140 Kev.) not only provides sufficient tissue penetration but also is readily collimated; and absence of beta radiation permits millicurie amounts of the radionuclide to be administered orally or by injection into the patient without harmful radiation dosage. Due to these physical characteristics, technetium-99m is frequently used in combination with appropriate carriers for in vivo diagnostic tests such as scintigraphic examinations of the liver, lungs, blood pool, bone and tumors. Because no operation is required for diagnosis, the popularity of this method has increased in recent years.

Chemically, technetium belongs to group VII-A of the Periodic Table of the Elements and there are many similarities between its chemistry and the chemistry of manganese and rhenium. In aqueous solution, the most stable form of technetium is the pertechnetate ion ($TcO_4^-$), which is similar to iodide in its biological distribution, thereby rendering it useful in scanning. Moreover, the ability of technetium to combine with other materials when reduced to lower oxidation states makes it useful both when chelated with an appropriate carrier for kidney or blood function studies and also when trapped physically as a colloid for liver studies or as a particle for lung studies. Since technetium-99m has such a short half-life, it is commonly extracted from its parent element, 2.7 day molybdenum-99, as required, via a generator wherein $^{99m}Tc$ is eluted from $^{99}Mo$. Moreover, technetium in the form of sodium pertechnetate in an isotonic saline solution is generally mixed with an appropriate carrier to label it for use in various scintigraphic examinations.

Various processes of preparing diagnostic agents labeled with technetium-99m have employed ferric chloride, ferrous sulfate, ferrous ascorbate, stannous chloride, stannous chloride and streptokinase or urokinase, including a combination of components such as gelatin, sodium thiosulfate, sodium perrhenate and an inorganic acid. In some of these processes, the non-radioactive carrier prepared had a relatively short shelf-life. This required each medical facility to maintain facilities and personnel to prepare the tracer material. Non-radioactive chelates, in particular diethylene-triaminepenta-acetic acid (DTPA), human serum albumin (HSA) and acid citrate dextrose (ACD) having an extended shelf life, have been prepared employing stannous chloride as a reducing agent.

SUMMARY OF THE INVENTION

It is an object of this invention to provide a method of preparing technetium-99m labeled radiodiagnostic agents well suited for lung and bone scanning applications. Another object of this invention is to provide a method of preparing non-radioactive carriers employing stannous tartrate. Still another object is to provide a simple and economical method of preparing non-radioactive carriers having a long shelf-life and which are useful as in the preparation of technetium-99m labeled radiodiagnostic agents. This and other objects will readily become apparent to those skilled in the art in the light of the teachings herein set forth. This invention is based on the discovery that stannous tartrate provides a superior reducing agent in the preparation of labeled technetium compounds and non-radioactive carrier precursors useful in preparing the technetium labeled compounds.

A characterizing feature of the method of this invention is contacting stannous tartrate with a sequestering agent selected from the group consisting of a phosphorus-containing compound which contains a P-O-P linkage and a diphosphonate which contains P-C-P bonds. Such sequestering agents provide suitable bone scanning agents after tagging with $^{99m}Tc$ and include the following phosphorus-containing compounds: (a) inorganic phosphates such as sodium pyrophosphate, sodium tripolyphosphate, sodium orthophosphate, sodium polyphosphate and the like, and (b) organic phosphonates such as 1-hydroxyethylidene-1, 1-disodium phosphonate, sodium methylene diphosphonate, the mono substituted salts of sodium methylene diphosphonate or sodium dichloromethylene diphosphonate, 1-hydroxyethylidene-1-mono-sodium phosphonate and the like. A particularly preferred organic phosphonate compound from this group is 1-hydroxyethylidene-1, 1-disodium phosphonate (hereinafter referred to as HEDSPA).

The method of this invention is also characterized when stannous tartrate is contacted with human serum albumin in forming the non-radioactive carrier, macro-aggregated albumin (hereinafter referred to as MAA). MAA is a particle formed containing stannous tartrate. In preparing the $^{99m}Tc$-labeled sequestering agent such as $^{99m}Tc$-labeled HEDSPA or the $^{99m}Tc$-labeled MAA, the non-radioactive carrier comprising the sequestering agent and stannous tartrate, e.g., HEDSPA-stannous tartrate, or MAA-stannous tartrate is contacted with $^{99m}Tc$ contained in the form of pertechnetate ion from $NaTcO_4$ in normal saline solution.

MAA or sequestering agents such as HEDSPA ordinarily will not complex with technetium as pertechnetate but will complex with a tin-reduced pertechnetate. In the method of this invention by use of stannous tartrate, technetium may be reduced from a $^+7$ oxidation state to a lower oxidation state suitable for complexing with technetium as pertechnetate. Moreover, the use of stannous tartrate provides a non-radioactive carrier more stable to oxidation as well as being suitable for mixing with a complexing agent. Generally, stannous compounds are easily oxidized to stannic compounds in aqueous solution. Moreover, in the absence of strongly complexing anions, tin having a $^+2$ oxidation state is extensively hydrolyzed in aqueous solution. The hydrolyzed and oxidized compounds of tin formed in aqueous solution produce insoluble compounds. These insoluble compounds prevent the reaction of tin in the preparation of a radiodiagnostic agent and such agent would go to the lungs or liver metabolically thus interfering with diagnostic applications. This problem has been overcome by the use of stannous ion chelated with tartrate. By chelating with tin, tartrate substantially pevents deleterious oxidation of tin and the formation of stannous ions in solution. Otherwise, oxidants such as peroxides, hydroxide radicals and the like, formed as a result of radiolysis, would consume ionized tin. In the method of this invention, however, this is prevented by employing stannous tartrate which is not strongly ionized in aqueous solution whereas stannous chloride is.

It has been found that stannous tartrate may be beneficially employed in the preparation of an improved MAA particle useful in lung scanning. Since the employment of stannous tartrate prevents hydrolysis, a more consistent MAA particle may be prepared. The MAA particle has fewer colloidal tin particles which can trap $^{99m}$Tc and cause an undesirable large liver uptake. Furthermore, the macroaggregated particule prepared according to this invention has a remarkably uniform particle size which gives superior lung to liver ratios. Additionally, the use of stannous tartrate in the method of this invention provides non-radioactive carrier solutions, such as HEDSPA-stannous tartrate and MAA-stannous tartrate, which have a long shelf-life since they are very stable and substantially not subject to oxidation or radiolysis when labeled with technetium-99m.

The macroaggregated particles prepared according to the method of this invention are sized between about 3 microns and about 150 microns in diameter, preferably between about 10 microns and about 90 microns in diameter, a majority being about 50 microns in diameter. The $^{99m}$Tc labeled MAA-stannous tartrate compound is useful in lung function studies. After injection into the patient, the macroaggregated particles are retained by the capillary system of the lungs, allowing a scintiphoto of the physiological vascular system of the lungs to be made. Macroaggregated particles of human serum albumin are non-toxic and readily digestible in the capillaries by the phagocytes. As a result, the obstruction of capillaries is of comparatively short duration.

Macroaggregated particles larger than 150 microns in diameter cause difficulties by blocking off large capillaries which is harmful to the pulmonary system. When macroaggregated particles are smaller than 3 microns in diameter, they pass through the capillaries directly to the liver. Moreover, even in the proper size range, the particles should be stable enough so that they do not break down and are not promptly released into the liver and spleen. Particles which pass immediately into the liver cause shadows and distort the scintiphoto of the lungs. Macroaggregated particles prepared according to the method of this invention and labeled with $^{99m}$Tc have been found to have a lung to liver ratio of particle distribution greater than about 100 to 1, i.e., less than about 1% of the particles passing into the liver. This percentage of particles passing into the liver is well below acceptable human tolerance levels.

In one aspect, this invention relates to a process for the preparation of a stable, non-radioactive carrier comprising stannous tartrate and a sequestering agent selected from the group consisting of a phosphorus-containing compound which contains a P-O-P linkage and a phosphonate which contains P-C-P bonds. Suitable sequestering agents include sodium polyphosphate, sodium pyrophosphate or any of a variety of phosphonates with hydroxyl, methyl, ethyl and chloro groups substituted for hydrogen on the carbon atom. As described hereinbefore, a preferred sequestering agent is HEDSPA having the following structure:

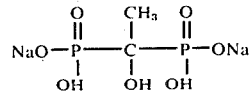

According to the method of this invention a sequestering agent as defined hereinabove such as HEDSPA is contacted with a sufficient amount of a nonoxidizing acid to form a solution having a pH from about 2 to about 7, preferably about 6.0. Suitable nonoxidizng acids include hydrochloric, acetic, sulfuric and phosphoric and the like. Preferably, a 1 Normal hydrochloric acid is employed. Stannous tartrate is dissolved in this solution and the resulting solution has a pH between about 2 and about 7, but preferably about 4. Preferably, stannous tartrate is added to the solution containing the sequestering agent such as a HEDSPA-solution in an amount between about 3 to 1 and 20 to 1 of sequestering agent such as HEDSPA to stannous tartrate on a weight basis. The final pH of the solution may be adjusted by using sodium hydroxide solution. The solution may be lyophilized at a temperature below about 0° C, preferably between about 0° C and −10° C when it is desirable to store it before use, or it may be used in liquid form for a short time.

$^{99m}$Tc labeled HEDSPA may be prepared by contacting the lyophilized or liquid product with a sufficient amount of a saline solution of Na$^{99m}$TcO$_4$ to form $^{99m}$Tc-HEDSPA solution.

In another aspect, this invention relates to a method of preparing a non-radioactive macroaggregated albumin product. A saline solution is acidified to a pH between about 2 and about 6, preferably about 5.5 with a sufficient quantity of a non-oxidizing acid. Suitable non-oxidizing acids include hydrochloric, acetic, sulfuric, phosphoric or the like. A preferred acid is hydrochloric acid. Stannous tartrate is dissolved in the solution and then Human Serum Albumin is added, or this order of addition may be reversed, if desired. The pH of the resulting solution may then be adjusted with the addition of a sufficient amount of sodium hydroxide to between 5 and 6, but preferably between about 5.5 and about 5.6. After adjusting the pH, the solution is heaed a predetermined time between about 20 minutes and about 40 minutes, preferably about 25 minutes, at a temperature sufficient to macroaggregate the albumin. This temperature may range between about 70° C and about 80° C, but preferably is about 74° C.

Preservatives may be used in the method of this invention, but are not necessary for the efficacy of the product. Suitable preservatives include thimerosal, parabens (methyl p-hydroxybenzoates and propyl p-hydroxybenzoates) and the like. Generally, the preservative may be added during the preparation of the stable, non-radioactive carrier product of this invention. The product may be prepared in the wet form or lyophilized at a temperature below about 0° C, preferably between about 0° C and about −10° C.

This stable, nonradioactive product of macroaggregated albumin formed as described hereinabove may be labeled with technetium-99m by contacting the lyophilized or liquid product with a sufficient amount of a saline solution of Na$^{99m}$TcO$_4$ to form $^{99m}$Tc macroaggregated albumin solution. The $^{99m}$Tc-labeled MAA product should have a radioactivity concentration of at least about 1 millicurie (mCi) per unit volume of solution. Typically, between about 0.5 ml and about 1 ml of solution would be administered to patients when using the solutions for radiodiagnostic testing purposes.

The following examples illustrate the invention:

EXAMPLE I

A nonradioactive carrier solution, MAA-stannous tartrate, was prepared in the following manner: The pH of 90ml of saline solution was adjusted to 4.0 with 0.2 N HCl. Then 50mg of stannous tartrate (200 μg) Sn$^{++}$/ml in final volume) was added to the solution which was stirred slowly to dissolve the stannous tartrate. Then 0.25 ml of 25% human serum albumin (HSA) was added. After 15 minutes incubation at a temperature of 21° C, the pH of the solution was adjusted to 5.5 with 0.5 N NaOH and the volume increased to 100 ml with saline solution. Then the stannous tartrate-HSA containing solution was aggregated at 74° C for 25 minutes into MAA-stannous tartrate. 0.6cc of the macroaggregates are aliquoted into 10cc serum vials and centrifuged. The supernatant solution is decanted.

Microscopic examination of the particles showed firm, elongated aggregates. The particles were between 20–50 microns with no particles under 10 or over 80 microns. Using 3 ml of low concentration $^{99m}$Tc, the lung to liver ratio in mice was measured to be 200 to 1.

The aggregates were tested for stability immediately after preparation and 6 ½ hours after preparation and the lung to liver ratio improved with little aggregation or change in particle size. A bioassay of mice showed lung to liver ratios of 200–300 to 1. To test the toxicity effects on mice, 0.6 ml of the aggregates (3 times normal injection) was injected with no ill effects observed in 24 hours. A lung clearance study was made on mice using the procedure employing stannous tartrate described hereinabove to produce the tagged macroaggregates and the results of this study are summarized in Table I below:

TABLE I

Lung Clearance on Mice of $^{99m}$Tc-MAA Prepared with Stannous Tartrate

| Time After Injection | Lung to Liver Ratios | % Remaining in Lungs |
|---|---|---|
| 15 min. | 500 to 1 | 98.7 |
| 30 min. | 72 to 1 | 94.9 |
| 60 min. | 23 to 1 | 92.2 |
| 90 min. | 23 to 1 | 85.7 |
| 2 hrs. | 3 to 1 | 50.8 |
| 3 hrs. | 3 to 1 | 52.7 |
| 4 hrs. | 1 to 2 | 16.1 |
| 5 hrs. | 1 to 1½ | 21.0 |
| 24 hrs. | — | 4.0 |

EXAMPLE II

Two parallel runs were made using the identical procedure in each case, except that stannous chloride was used as the reducing agent in one run and in the other run stannous tartrate was used as the reducing agent in the preparation of a MAA lung scanning agent. The following procedure was used:

In one run 30mg of stannous chloride in 2 ml (approximately 0.24 mg Sn$^{++}$/ml) 0.1 N HCl was added to 90 ml of normal saline solution. In the other run, 50mg of stannous tartrate (approximately 0.24 mg Sn$^{++}$/ml) in 2 ml of 0.1 N HCl was added to 90 ml of normal saline solution. 0.25 ml of 25% human serum albumin (HSA) was then added to the saline solution. The pH of the solution was adjusted to 5.5 with 0.1 N NaOH. After the solution was incubated at a temperature of 21° C for 15 minutes, the albumin was denatured at 74° C for 25 minutes. 0.6 ml aliquots of macroaggregates in saline solution prepared as described above were transferred to 10 ml serum vials. The vials were centrifuged and the supernate decanted.

Use of the stannous tartrate reducing agent produced macroaggregated albumin particles which make a superior lung scanning agent. It did not produce large particles and the lung to liver ratio was very good. It is necessary that the lung to liver ratio be at least 20 to 1 with no particles greater than 150 microns in order that the lung scanning agent meet standard specifications. A comparison between MAA made using stannous chloride and stannous tartrate indicated MAA made using stannous chloride could not meet these standard specifications. A comparison between the two systems is summarized in Table II below:

Table II

Comparison Study Between Stannous Chloride and Stannous Tartrate in the Preparation of a MAA Lung Scanning Agent

| Comparison Test | Stannous Chloride | Stannous Tartrate |
|---|---|---|
| Lung to Liver Ratio | 12 to 1 | 200 to 1 –295 to 1 |
| % Activity in Lung | 94 | 96.5 |
| *Total Number of particles/ml | 200,000 | 3,000,000 |
| Particle Size | Majority of particles between 150–200 microns | More than 80% between 30–70 microns less than 4% under 10 microns none over 100 microns |
| Toxicity in Mice | Labored breathing, sluggishness, probably death would result | No reaction |

*This number represents total number of particles before tagging with 3ml of $^{99m}$Tc.

A further comparison was made using 0.6 ml aliquots of macroaggregates in saline solution prepared with stannous tartrate as described hereinabove in this example and placed in serum vials, centrifuged and decanted. In one group, the MAA particles in the vials were lyophilized and stored under refrigeration. In another group, the MAA particles in the vials were refrigerated only, but not lyophilized in order to measure the effect of lyophilizing on shelf-life stability.

3 ml of low concentration $^{99m}$Tc was added to each vial containing MAA stannous tartrate chelate. The vials were shaken and incubated for 30 minutes at a temperature of 21° C. Although the freeze-dried samples gave excellent lung to liver ratios if used immediately after preparation, on standing, there was a deterioration of the protein. This deterioration is believed to be caused by residual sodium chloride present in solution. After 18 days, the freeze-dried samples gave unsatisfactory lung to liver ratios. Moreover, the freeze-dried samples had the further disadvantage of adherence to the bottom of the vials after storage, making it difficult to resuspend the particles. In contrast, the centrifuged samples did not have this sticking problem and gave good lung to liver ratios even after 18 days. The results are summarized in Table III below:

Table III

Shelf-Life Study on Freeze-Dried and Centrifugated MAA Particles

| Time After Preparation (Days) | Lung to Liver Ratio | |
| --- | --- | --- |
| | Freeze-Dried After Centrifugation | Centrifuged Only |
| 4 | 245 to 1 | 220 to 1 |
| 8 | 129 to 1 | 129 to 1 |
| 9 | 73 to 1 | 91 to 1 |
| 10 | 85 to 1 | 320 to 1 |
| 11 | 46 to 1 | 166 to 1 |
| 15 | 28 to 1 | 318 to 1 |
| 18 | 25 to 1 | 216 to 1 |

In still another group, the MAA particles prepared with stannous tartrate and tagged with $^{99m}$Tc as described hereinabove were injected into 4 mice. The mice were placed in a metabolism cage and collective urine samples were periodically counted and urine clearance of $^{99m}$Tc activity was compared to injected activity. There was a rapid urine clearance of the $^{99m}$Tc activity from the mice which was comparable to that of iodinated MAA. The results are summarized in Table IV below:

TABLE IV

Urine Clearance of $^{99m}$Tc Activity in Mice After Injection of $^{99m}$Tc MAA

| Time (hours) | % of Injected Activity* in Urine |
| --- | --- |
| 1 | 4.1 |
| 2 | 8.5 |
| 3 | 12.1 |
| 4 | 16.4 |
| 5 | 21.7 |
| 6 | 31.0 |
| 24 | 54.0 |

*Four Mice

EXAMPLE III

A macroaggregated albumin-stannous tartrate chelate useful in lung scanning applications may be prepared according to this invention as follows: A minimum of 20 mg and a maximum of 100 mg of stannous tartrate is dissolved in approximately 2 ml of 0.1N HCl and 90 ml of normal saline solution. 0.25 ml of 25% human serum albumin is added and the pH is adjusted to 5.5 with 0.1N NaOH. 8 ml of normal saline is added to this solution and the pH readjusted to 5.5 with 0.1N HCl if necessary. This solution is filtered through a 0.22 micron filter. The filtered solution is diluted to approximately 110 ml with normal saline and placed in a temperature controlled bath at 74° C for 25 minutes. 0.6 ml aliquots are transferred to 10cc vials and centrifuged for 1.5 minutes. The supernate is decanted. To prepare the $^{99m}$Tc-MAA particles for lung scanning, 3 ml of pertechnetate (Na $^{99m}$TcO$_4$) saline solution is added to the vial containing the centrifuged particles and, after 30 minutes incubation at a temperature of 21°C, the radiodiagnostic product is ready for use.

Reagents prepared as described hereinabove in this example shown lung-to-liver ratios of greater than 200 to 1 in bioassay tests in mice. Binding of the $^{99m}$Tc to the particles was greater than 90% as determined by paper chromatography. Stability of the MAA-stannous tartrate particles (non-radioactive chelate) was measured to be at least 120 days and the stability of the $^{99m}$Tc-tagged MAA particles (radiodiagnostic agent) was greater than 6 hours. More than 80% of the particles were in the 30–70 micron size range with no particles having a size greater than 100 microns.

EXAMPLE IV

A number of samples of $^{99m}$Tc-tagged MAA particles were prepared according to the method described hereinabove in Example III. Various preservatives were added during the preparation of some of the samples. It may be desirable to add a preservative to the $^{99m}$Tc-tagged MAA particles. Since the albumin particles are an ideal matrix for growing bacteria, a sterility problem may arise during long storage periods even if storage is in sealed vials. It has been found that thimerosal may be added as a preservative without affecting the quality of the MAA paticles. When 0.2 ml (0.4mg) of thimerosal (merthiolate) was added to a sample solution prepared as described hereinabove, before the step wherein the aggregregates were precipitated, the lung to liver ratio was not affected. In addition, MAA particles were prepared as described hereinabove with parabens (methyl and propyl p-hydroxybenzoates) as a preservative. Parabens are effective in low concentrations against fungi and certain types of bacteria. A combination of 0.18% methyl ester and 0.02% propyl ester was used. The parabens were made up in this concentration in normal saline solution. After MAA particles, prepared as described hereinabove, were centrifuged and the supernate discarded, one drop of this preservative was added to the wet MAA particles. In MAA particles with this preservative, a bioassay in mice showed a lung to liver ratio of 400: 1 immediately after preparation, but a lung to liver ratio of 170: 1 after 5 days storage.

The samples were tagged with 3 ml of low concentration $^{99m}$Tc (10mCi/ml) after being stored for periods of time and lung to liver ratio and per cent uptake in the lung was measured to determine the effect of shelf-life on the usefulness of the MAA particles. The results of these shelf-life studies of a number of samples both with and without preservatives is summarized in Table V below:

Table V

Shelf-Life Studies on MAA-Stannous Tartrate

| Sample | Preservative | Time After Preparation (Days) | Bioassay in Mice | |
| --- | --- | --- | --- | --- |
| | | | Lung % Uptake | Lung to Liver Ratio |
| 1 | — | 5 | 98 | 350:1 |
| 2 | — | 89 | 95 | 160:1 |
| 3 | — | 245 | 91.4 | 40:1 |
| 4 | — | 66 | 97.4 | 200:1 |
| 5 | thimerosal | 64 | 97 | 400:1 |
| 6 | thimerosal | 131 | 98.3 | 325:1 |
| 7 | parabens | 202 | 81 | 47:1 |
| 8 | parabens | 121 | 98.3 | 300:1 |

Table V-continued

Shelf-Life Studies on MAA-Stannous Tartrate

| Sample | Preservative | Time After Preparation (Days) | Bioassay in Mice Lung % Uptake | Lung to Liver Ratio |
|---|---|---|---|---|
| 9 | parabens | 92 | 95.3 | 150:1 |
| 10 | parabens | 59 | 94.3 | 180:1 |

EXAMPLE V

MAA particles prepared as described in Example IV with paraben preservative were placed in 10cc serum vials and diluted with 1, 3, and 5 ml of low concentration $^{99m}$Tc. A microscopic examination of the particles immediately after dilution and 30 minutes, 1 hour, 2 hours and 4 hours after preparation indicated no breakdown of particle size on any of the samples. When repeating this procedure and now adding 5 ml of saline to each vial in addition to the 1, 3 and 5 ml of low concentration $^{99m}$Tc, the sample diluted to 10 ml broke down into smaller particles after 30 minutes and the vial with 8 ml broke down in particle size after 1 hour. According to the process of this invention, the dilution of the MAA particles must be limited to 6 ml total volume.

EXAMPLE VI

Using the procedure described hereinabove in Example III for preparing a macroaggregated albumin-stannous tartrate chelate, nine runs were made using 5, 10, 20, 30, 40, 60, 100, 150 and 250 mg of stannous tartrate, respectively in the runs. Each set of MAA particles prepared was tested by bioassay in mice, chromatographic analysis and microscopic examination. The bioassay results indicated that the minimum workable concentration was about 10 mg and the maximum workable concentration with about 150 mg. It is preferred, however, that the quantity of stannous tartrate which may be used in the preparation of the MAA particles according to the teachings of this invention be between about 30 mg and about 100 mg and more preferably about 50 mg. Chromotographic analysis indicated that binding increased with increased stannous tartrate concentration. It is preferred, however, that at least 30 mg of stannous tartrate be used to obtain a binding of at least about 95%. Microscopic examination indicated that when concentrations of stannous tartrate between about 5 mg to about 30 mg were used, the MAA particles produced were very firm. When the concentration of stannous tartrate used was increased, the particles became softer. After 100 mg concentration of stannous tartrate, the MAA particles diminished in size and when 250 mg of stannous tartrate were used, there were many particles below 5 microns.

EXAMPLE VII

A batch of HEDSPA-stannous tartrate was prepared by the following procedure. 100 ml (5mg/ml) of HEDSPA were added to a 500 ml flask and purged with $N_2$ (pH 9.0). The pH was adjusted to 6.0 with 0.2 N HCl. 116 mg of stannous tartrate was added and mixed until dissolved. The solution was diluted to 200 ml with distilled water, transferred into 10 ml serum vials in 1 ml amounts and lyophilized; 3 ml of high concentration $^{99m}$Tc (30mCi/ml) in the form of sodium pertechnetate ($Na^{99m}TcO_4$) was added to the dried contents of one vial and shaken for 1 minute. Chromatographic analysis indicated a binding of 95% immediately after preparation. Autoradiographs indicated excellent bone uptake in mice and a bioassay in mice measured 92% of the activity in the body with the organs removed. The batch of HEDSPA-stannous tartrate had a pH of 4.0 and had greater stability at this pH than an identical batch preparation using stannous chloride instead of stannous tartrate. After 37 days, the bioassay in mice indicated good bone uptake and chromatographic results showed greater than 99% bound $^{99m}$Tc. The results are summarized in Table VI below:

TABLE VI

Shelf-Life Stability of HEDSPA-Stannous Tartrate*

Bioassay in Mice**
% of Injected Activity

| Days After Preparation | Stomach and Intestines | Kidneys | Liver | Body (Organs Removed) | % Bound Chromotographic Analysis |
|---|---|---|---|---|---|
| 3 | 7.2 | 2.0 | 0.8 | 89.9 | >99% |
| 4 | 3.3 | 1.8 | 1.0 | 93.8 | >99% |
| 12 | 5.2 | 2.0 | 1.0 | 91.4 | >99% |
| 21 | 5.2 | 1.3 | 0.8 | 92.7 | >99% |
| 37 | 4.4 | 1.6 | 0.6 | 93.0 | >99% |

*Reconstituted at pH 4.0 with 3 ml High Concentration $^{99m}$Tc (3mCi/ml)
**Average of two mice.

The blood clearance in a rabbit and mice is shown in Table VII below:

TABLE VII

Blood Clearance of $^{99m}$Tc-HEDSPA-Stannous Tartrate*
In Mice and In a Rabbit

| Mice | | Rabbit | |
|---|---|---|---|
| Time After Injection | % Activity Remaining in Blood** | Time After Injection | % Activity*** Remaining in Blood |
| 10 min. | 4.8 | 3 min. | 46.4 |
| 20 min. | 3.7 | 20 min. | 9.6 |
| 30 min. | 1.3 | 33 min. | 10.9 |

TABLE VII-continued

Blood Clearance of $^{99m}$Tc-HEDSPA-Stannous Tartrate* In Mice and In a Rabbit

| Mice | | Rabbit | |
|---|---|---|---|
| Time After Injection | % Activity Remaining in Blood** | Time After Injection | % Activity*** Remaining in Blood |
| 1 hr. | 0.7 | 60 min. | 4.0 |
| 2 hr. | 0.4 | 130 min. | |
| 3 hr. | 0.1 | 195 min. | 1.9 |
| 4 hr. | 0.2 | | |

*Reconstituted at pH 4.0 with 3 ml High Concentration $^{99m}$Tc (30mCi/ml)
**Average of 2 mice
***One rabbit The results summarized in Table VII above indicate that the activity (in mice and a rabbit) reaches a constant level after 2 hours permitting scanning of the patient from about 1 to about 2 hours after injection. Continued shelf-life studies indicate satisfactory results were obtainable after 200 days storage.

EXAMPLE VIII

Using the same procedure as described in Example VII, four batches of HEDSPA-stannous tartrate were prepared. In the preparation of these four batches, however, 0.5N NaOH was used to adjust the pH of the final products to 4.0, 5.0, 6.0 and 7.0, respectively. Then the batches were each aliquoted into vials and lyophilized. Chromotographic analysis indicated a binding greater than 99% immediately after preparation. Autoradiographs on mice showed excellent bone uptake and the results of a bioassay on mice are summarized in Table VIII below:

TABLE VIII

Comparison of Lyophilized HEDSPA-Stannous Tartrate at Various pH Concentrations

| | Bioassay in Mice, % of Injected Activity | | | |
|---|---|---|---|---|
| Organ | pH 4.0 | pH 5.0 | pH 6.0 | pH 7.0 |
| Carcass | 93.4 | 91.4 | 92.6 | 90.2 |
| Intestines and Stomach | 2.9 | 3.2 | 3.1 | 3.8 |
| Liver and Spleen | 1.2 | 2.1 | 1.7 | 1.7 |
| Kidneys | 1.9 | 2.2 | 1.7 | 2.6 |
| Heart-Lungs | 0.7 | 1.0 | 1.0 | 1.7 |

All pH ranges showed similar uptake and similarly satisfactory results were obtained after 55 days storage of the four samples.

EXAMPLE IX

Using the following procedures, two non-radioactive chelates, HEDSPA-stannous chloride and HEDSPA-stannous tartrate were prepared from comparison of stability and shelf-life.

A batch of 150 ml of HEDSPA-stannous chloride, the final reagent, was prepared as follows: 75 ml of HEDSPA (5mg/ml) were added to a 500 ml flask which was purged with nitrogen gas. 53.8cc of 0.2 N HCl were added to the flask which was purged with nitrogen gas again for about 2 hours. 3.7 ml of stannous chloride solution in 0.2N HCl (10.4mg $Sn^{++}$/ml) were added to the flask and mixed. 14 ml of 1.0 N NaOH was added to the flask and mixed so that the final reagent had a pH of 4.0 (0.25mg $Sn^{++}$/ml). 1 ml of the final reagent was dispensed into 10 ml serum vials which were placed in a freeze dryer and lyophillized at −40° C and 200 microns of Hg vacuum for 48 hours.

A batch of 200 ml of the final reagent, HEDSPA-stannous tartrate, was prepared as follows: 100 ml of HEDSPA (5 mg/ml) were added to a 250 ml flask which was purged with nitrogen gas. The pH was adjusted to 6.0 with 0.2N HCl. 116 mg of solid stannous tartrate was added to the flask and mixed until dissolved. The solution in the flask was diluted to 200 ml with distilled water until the solution contained 0.25 mg $Sn^{++}$/ml and had a final pH of 4.0. 1 ml of the final reagent was dispensed into 10 ml serum vials which were placed in a freeze dryer and lyophillized at −40° C and 200 microns of Hg vacuum for 48 hours.

The two final reagents were analyzed immediately and stored for various time periods. A technetium-99m radiodiagnostic agent useful for bone scanning was prepared by the addition of 3 ml of sodium pertechnetate (Na$^{99m}$TcO$_4$) containing 30 mCi of $^{99m}$Tc to the final reagents, respectively, which were then shaken for 1 minute. The % binding efficiency of the chemical labeling procedure and stability of the preparation were determined by ascending paper chromotography using Whatman 1 paper strips in 85% methanol and scanning on a radiochromatographic scanner. The bioassay in mice was determined by injecting 0.2 ml into the tail veins of mice and sacrificing them after 1 hour uptake times. Table IX below summarizes that data:

TABLE IX

Shelf-Life Study on HEDSPA - Sn-Cl$_2$ and HEDSPA-Sn-Tartrateeat pH 4.0

| | Time After Preparation (Days) | *Bioassay in Mice % of Injected Activity | | | | | |
|---|---|---|---|---|---|---|---|
| | | % Binding | Body | Intestines | Liver | Kidney | Heart and Lungs |
| STANNOUS CHLORIDE | 1 | 99 | 81.4 | 4.1 | 0.7 | 2.0 | 0.2 |
| | 5 | 93.5 | 86.5 | 7.5 | 1.8 | 3.4 | 0.3 |
| | 8 | 91.4 | 93.8 | 3.1 | 1.1 | 1.9 | 0.2 |
| | 21 | 21.8 | 33.9 | 33.6 | 26.4 | 26.4 | 1.0 |
| | 35 | 3.3 | NO BIOASSAY PERFORMED | | | | |
| STANNOUS TARTRATE | 3 | 99 | 89.9 | 7.2 | 0.8 | 2.0 | 0.2 |
| | 4 | 99 | 93.8 | 3.3 | 1.0 | 1.8 | 0.2 |
| | 12 | 99 | 91.4 | 5.2 | 1.0 | 2.0 | 0.4 |
| | 21 | 99 | 92.7 | 5.2 | 0.8 | 1.2 | 0.1 |
| | 37 | 99 | 93.0 | 4.4 | 0.6 | 1.6 | 0.3 |
| | 50 | 99 | 93.2 | 2.7 | 1.0 | 2.6 | 0.5 |

TABLE IX-continued

Shelf-Life Study on HEDSPA - Sn-Cl₂ and HEDSPA-Sn-Tartrateeat pH 4.0

| Time After Preparation (Days) | % Binding | *Bioassay in Mice % of Injected Activity | | | | |
|---|---|---|---|---|---|---|
| | | Body | Intestines | Liver | Kidney | Heart and Lungs |
| **78 | 99 | 94.6 | 1.86 | 0.81 | 1.72 | 0.21 |

*Average of two mice, 1 hour uptake.
**Average of three mice, 0.2cc injection

The results of Table IX above indicates that HEDSPA-SnCl₂ at pH 4.0 loses its binding capacity between about 8 and about 21 days, rendering it undesirable as a non-radioactive chelate intermediate in the production of a technetium-99m labeled radiodiagnostic agent due to its short shelf-life. This is reinforced by the results of the bioassay on mice wherein the liver uptake after 21 days storage was undesirably high. In contrast, the HEDSPA-stannous tartrate at pH 4.0 retained its binding capacity after 78 days with little or no uptake in the liver. In still another shelf-life study, a batch of lyophillized HEDSPA-stannous tartrate at pH 4.0 was reconstituted using 3 ml of high concentration $^{99m}$Tc with satisfactory bioassay and binding results.

EXAMPLE X

Using the procedure described in Example VII, a batch of HEDSPA-stannous tartrate was prepared for comparison with a non-radioactive reagent useful in bone scanning and commercially available from Diagnostic Isotopes, Inc., stannous diphosphonate. Each product was reconstituted with 3 ml of high concentration $^{99m}$Tc (30 mCi/ml). Chromotographic analysis and bioassay tests were performed on the two reagents. The HEDSPA-stannous tartrate prepared as described hereinabove had better binding of the $^{99m}$Tc. The low uptake in the intestines and kidneys using the technetium-99m labeled bone scanning agent, $^{99m}$Tc-HEDSPA prepared using stannous tartrate, in relation to the high uptake in the intestines and kidney when the technetium-99m labeled bone scanning agent commercially available from Diagnostic Isotopes, Inc., stannous diphosphonate, was used indicated that there was less free pertechnetate when stannous tartrate was used as the reducing agent. The use of stannous tartrate, moreover, yielded a product with more stability than the Diagnostic Isotopes, Inc. product. The results of these tests are summarized in Table X below:

TABLE X

Comparison Study Between Two Radiodiagnostic Products Useful in Bone Scanning

| Organ | Bioassay in Mice* % of Total Activity | |
|---|---|---|
| | $^{99m}$Tc-HEDSPA Product (using Stannous Tartrate) | Diagnostic Isotopes, Inc. Product (using Stannous Chloride) |
| Carcass | 95.5 | 88.1 |
| Intestines | 1.8 | 6.5 |
| Kidneys | 1.8 | 2.0 |
| Liver | 0.8 | 2.5 |
| Heart-Lungs | 0.2 | 0.8 |

*0.2cc injection, 2 hour uptake time.

| | | |
|---|---|---|
| Chromotographic Analysis | 99% bound | 93.6% bound |
| pH of reconstituted product | 4.0 | 6.5 |
| Concentration of diphosphonate | 2.5mg | 5mg |
| Concentration of stannous | 0.25mg | 0.25mg |

EXAMPLE XI

Four salts of stannous compounds were each dissolved in a solution of 40 ml of saline and 1 ml of 1N HCl which was purged with nitrogen. The stannous concentration was measured and then the solution was subjected to oxidation conditions by bubbling air through the solution for 2.5 hours. The stannous concentration was again measured. The results indicated that stannous tartrate is much more stable to air oxidation than stannous chloride. Moreover, the presence of tartaric acid does not significantly improve the stability of the stannous chloride, even when present in excessive amounts. The results are summarized in Table XI below:

TABLE XI

Comparison Tests on the Stability of Stannous Compounds Air Oxidation

| Salt Sample | Stannous Concentration Before Aeration (mg/ml) | Stannous Concentration After Aeration (mg/ml) | % Stannous tin remaining |
|---|---|---|---|
| 1. Stannous Chloride + Tartaric Acid (Equivalent amount | | | |

TABLE XI-continued

Comparison Tests on the Stability of Stannous Compounds Air Oxidation

| Salt Sample | Stannous Concentration Before Aeration (mg/ml) | Stannous Concentration After Aeration (mg/ml) | % Stannous tin remaining |
|---|---|---|---|
| of tartaric) | 10.8 | 6.0 | 55.5 |
| 2. Stannous Chloride + Tartaric Acid (twice equivalent amount of tartaric) | 10.4 | 4.2 | 40.4 |
| 3. Stannous Chloride | 9.3 | 3.6 | 38.7 |
| 4. Stannous Tartrate | 18.0 | 17.0 | 94.5 |

EXAMPLE XII

Six salts of stannous compounds were each dissolved in 98 ml of saline containing 2 ml 1N HCl. The solutions were analyzed in order to measure the stannous ion concentration and then were subjected to oxidation conditions by bubbling air through the solutions for one hour. The solutions were analyzed again. The results indicated that stannous tartrate is more stable than stannous chloride with tartrate or citrate ion present. Table XII below summarized the results:

TABLE XII

Comparison Tests on the Stability of Various Stannous Compounds to Air Oxidation

| Salt Sample | Stannous Concentration Before Aeration (mg/ml) | Stannous Concentration After Aeration (mg/ml) | % Not Oxidized tin |
|---|---|---|---|
| 1. Stannous Chloride | 0.138 | 0.085 | 61.6 |
| 2. Stannous Tartrate | 0.247 | 0.213 | 86.2 |
| 3. Stannous Chloride + Stannous Tartrate | 0.151 | 0.003 | 19.8 |
| 4. Stannous Chloride + Potassium-Sodium Tartrate | 0.166 | 0.002 | 15.0 |
| 5. Stannous Chloride + Sodium Oxalate | 0.134 | 0.002 | 15.0 |
| 6. Stannous Chloride + Sodium Citrate | 0.196 | 0.092 | 47.0 |

Those skilled in the art will appreciate that the particular examples of this invention described hereinabove are intended to be illustrative only and are not intended to limit the scope of the invention.

What is claimed is:

1. A method of preparing a stable, non-radioactive carrier comprising:
   a. contacting a sequestering agent with a sufficient amount of a non-oxidizing acid to form a solution containing said sequestering agent having a pH from about 2 to about 7, said sequestering agent selected from the group consisting of a phosphorus-containing compound which contains a P-O-P linkage and a phosphonate which contains P-C-P bonds; and
   b. dissolving stannous tartrate in said solution to form a stannous tartrate containing solution having a pH between about 2 and about 7.

2. A method as defined in claim 1 wherein said non-oxidizing acid is selected from the group consisting of hydrochloric, acetic, sulfuric and phosphoric acid.

3. A method as defined in claim 1 wherein said sequestering agent is selected from the group consisting of sodium pyrophosphate, sodium tripolyphosphate, sodium orthophosphate, sodium polyphosphate, 1-hydroxyethylidene-1, 1-disodium phosphonate (HEDSPA), sodium methylene disphosphonate, the mono substituted salts of sodium methylene disphosphonate, the mono substituted salts of sodium dichloromethylene diphosphonate and 1-hydroxyethylidene-1-monosodium phosphonate.

4. A method as defined in claim 3 wherein said sequestering agent is HEDSPA.

5. A method as defined in claim 4 wherein the pH of said HEDSPA-containing solution is about 6 and the pH of said stannous tartrate containing solution is about 4.

6. A method as defined in claim 4 wherein said stannous tartrate is added to said HEDSPA-containing solution in an amount between about 3 to 1 and 20 to 1 of HEDSPA to stannous tartrate on a weight basis.

7. A method as defined in claim 1 wherein said stannous tartrate containing solution is lyophilized at a temperature below about 0° C.

8. A method as defined in claim 7 wherein said lyophilization temperature is between about 0° C and −10° C.

9. A method as defined in claim 1 wherein said stannous tartrate containing solution is contacted with a sufficient amount of a saline solution of $Na^{99m}TcO_4$ to form a $^{99m}Tc$-labeled solution containing said sequestering agent.

10. A method of preparing a stable, non-radioactive macroaggregated albumin carrier comprising:

a. contacting a saline solution with a sufficient amount of a non-oxidizing acid to adjust the pH of said solution to between about 2 and about 6;

b. introducing stannous tartrate and human serum albumin into said solution to form a stannous tartrate containing solution;

c. adding a sufficient amount of sodium hydroxide to adjust the pH of said stannous tartrate containing solution to between about 5 and about 6;

d. heating said pH adjusted solution a predetermined time at a temperature sufficient to macroaggregate the albumin, said macroaggregated albumin comprising particles sized between about 3 microns and about 150 microns in diameter.

11. A method as defined in claim 10 wherein said nonoxidizing acid is selected from the group consisting of hydrochloric, acetic, sulfuric and phosphoric.

12. A method as defined in claim 11 wherein said nonoxidizing acid is hydrochloric acid.

13. A method as defined in claim 10 wherein the pH of said saline solution is about 5.5 and the pH of said stannous tartrate containing solution is between about 5.5 and about 5.6.

14. A method as defined in claim 10 wherein said predetermined time is between about 20 minutes and about 40 minutes and said temperature is between about 70° C and about 80° C.

15. A method as defined in claim 14 wherein said predetermined time is about 25 minutes and said temperature is about 74° C.

16. A method as defined in claim 10 further including the step of adding a preservative to said stannous tartrate containing solution, said preservative selected from the group consisting of thimerosal, methyl and propyl p-hydroxy benzoates.

17. A method as defined in claim 10 wherein said stannous tartrate containing solution is lyophilized at a temperature below about 0° C.

18. A method as defined in claim 17 wherein said lyophilization temperature is between about 0° C and −10° C.

19. A method as defined in claim 10 wherein said particles are sized between about 10 microns and about 90 microns in diameter, a majority being about 50 microns in diameter.

20. A method as defined in claim 10 wherein said stannous tartrate containing solution is contacted with a sufficient amount of a saline solution of $Na^{99m}TcO_4$ to form a $^{99m}Tc$-labeled macroaggregated albumin solution.

21. A stable, non-radioactive carrier comprising stannous ion chelated with tartrate and a sequestering agent selected from the group consisting of a phosphorus-containing compound which contains a P-O-P linkage and phosphonate which contains P-C-P bonds, said carrier having a pH between about 2 and about 7.

22. A carrier as defined in claim 21 wherein said sequestering agent is an inorganic phosphate.

23. A carrier as defined in claim 21 wherein said sequestering agent is an organic phosphonate.

24. A carrier as defined in claim 23 wherein said organic phosphonate is 1-hydroxyethylidene-1, 1-disodium phosphonate (HEDSPA).

25. A carrier as defined in claim 24 wherein the pH of said carrier is about 4.

26. A carrier as defined in claim 24 wherein on a weight basis, the ratio of said HEDSPA to said stannous ion chelated with tartrate is between about 3 to 1 and 20 to 1.

27. A radiodiagnostic agent suitable for bone scanning comprising stannous ion chelated with tartrate, a sequestering agent selected from the group consisting of a phosphorus-containing compound which contains a P-O-P linkage and a phosphonate which contains P-C-P bonds, and a saline solution of $Na^{99m}TcO_4$.

28. A stable, non-radioactive macroaggregated albumin carrier, said carrier comprising a macroaggregated human serum albumin and stannous ion chelated with tartrate, said carrier having a pH between about 5 and about 6, said macroaggregated albumin comprising particles sized between about 3 microns and about 150 microns in diameter.

29. A carrier as defined in claim 27 wherein the pH of said carrier is between about 5.5 and about 5.6.

30. A carrier as defined in claim 27 wherein said particles are sized between about 10 microns and about 90 microns, the majority being about 50 microns in diameter.

31. A radiodiagnostic agent suitable for lung scanning comprising a macroaggregated human serum albumin, stannous ion chelated with tartrate and a saline solution of $Na^{99m}TcO_4$.

* * * * *